United States Patent
Kimbara et al.

(10) Patent No.: US 9,090,615 B2
(45) Date of Patent: Jul. 28, 2015

(54) ADAMANTYL DERIVATIVES AS CANNABINOID RECEPTOR 2 AGONISTS

(71) Applicant: Hoffmann-La Roche Inc., Little Falls, NJ (US)

(72) Inventors: Atsushi Kimbara, Shizuoka (JP); Uwe Grether, Efringen-Kirchen (DE); Matthias Nettekoven, Grenzach-Wyhlen (DE); Bernd Puellmann, Aesch (CH); Mark Rogers-Evans, Bottmingen (CH); Tanja Schulz-Gasch, Ziefen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/578,935

(22) Filed: Dec. 22, 2014

(65) Prior Publication Data

US 2015/0111886 A1 Apr. 23, 2015

Related U.S. Application Data

(63) Continuation of application No. PCT/EP2013/063773, filed on Jul. 1, 2013.

(30) Foreign Application Priority Data

Jul. 4, 2012 (EP) .................................... 12174968

(51) Int. Cl.
| | |
|---|---|
| C07D 471/04 | (2006.01) |
| C07D 217/04 | (2006.01) |
| C07D 215/08 | (2006.01) |
| C07D 215/233 | (2006.01) |
| C07D 215/50 | (2006.01) |
| C07D 215/54 | (2006.01) |
| C07D 215/14 | (2006.01) |
| C07D 265/36 | (2006.01) |
| C07D 209/08 | (2006.01) |

(52) U.S. Cl.
CPC ............ *C07D 471/04* (2013.01); *C07D 209/08* (2013.01); *C07D 215/08* (2013.01); *C07D 215/14* (2013.01); *C07D 215/233* (2013.01); *C07D 215/50* (2013.01); *C07D 215/54* (2013.01); *C07D 217/04* (2013.01); *C07D 265/36* (2013.01)

(58) Field of Classification Search
None
See application file for complete search history.

(56) References Cited

U.S. PATENT DOCUMENTS

2012/0053201 A1* 3/2012 Blackburn et al. ............ 514/300

OTHER PUBLICATIONS

Nettekoven et al., "Highly potent and selective cannabinoid receptor 2 agonists: Initial hit optimization of an adamantyl hit series identified from high-through-put screening" Bioorganic & Medicinal Chemistry Letters 23(5):1171-1181 (Jan. 23, 2013).

* cited by examiner

*Primary Examiner* — Timothy R Rozof
(74) *Attorney, Agent, or Firm* — Mark D. Kafka

(57) ABSTRACT

The invention relates to a compound of formula (I)

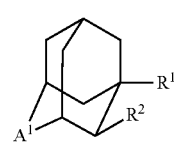

(I)

wherein $A^1$, $R^1$ and $R^2$ are defined as in the description and in the claims. The compound of formula (I) can be used as a medicament.

23 Claims, No Drawings

ADAMANTYL DERIVATIVES AS CANNABINOID RECEPTOR 2 AGONISTS

This application is a continuation application of International Application No. PCT/EP2013/063773, filed Jul. 1, 2013, which claims priority to EP 12174968.3, a European application filed Jul. 4, 2012, each of which is incorporated herein by reference in its entirety.

The present invention relates to organic compounds useful for therapy and/or prophylaxis in a mammal, and in particular to compounds that are preferential agonists of the Cannabinoid Receptor 2.

The invention relates in particular to a compound of formula (I)

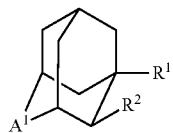

(I)

wherein
$A^1$ is —$CH_2$— or —$C(O)$—;
one of $R^1$ and $R^2$ is hydrogen and the other one is -$A^2$-C(O)—$R^3$;
$A^2$ is —NH— or absent;
$R^3$ is (A), (B) or (C);

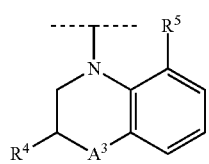

(A)

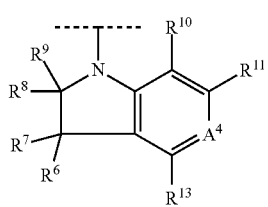

(B)

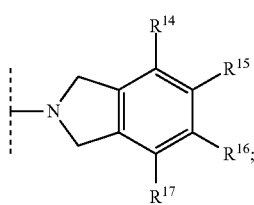

(C)

$A^3$ is —$CR^{18}R^{19}$—, —$NR^{20}$— or —$C(O)$—;
$A^4$ is nitrogen or —$CR^{12}$—;
$R^4$ is hydrogen or alkoxycarbonyl;
$R^5$ is hydrogen or alkyl;
$R^6$ and $R^7$ are independently selected from hydrogen and alkyl;
$R^8$ and $R^9$ are independently selected from hydrogen and alkyl;
$R^{10}$, $R^{11}$, $R^{12}$ and $R^{13}$ are independently selected from hydrogen, alkyl, nitro, fluoro, chloro, haloalkyl and alkoxy, provided that they are not all hydrogen at the same time;
or $R^{13}$ is alkoxycarbonyl and $R^{10}$, $R^{11}$ and $R^{12}$ are all hydrogen at the same time;
or $R^{10}$, $R^{11}$, $R^{12}$ and $R^{13}$ are all hydrogen at the same time, provided that:
at least two of $R^6$, $R^7$, $R^8$ and $R^9$ are alkyl and the other ones are hydrogen;
or $A^1$ is —C(O)—;
or $R^1$ is hydrogen and $R^2$ is is -$A^2$-C(O)—$R^3$;
$R^{14}$ and $R^{17}$ are independently selected from hydrogen and halogen;
$R^{15}$ and $R^{16}$ are independently selected from hydrogen, morpholinyl and halogen;
one of $R^{18}$ and $R^{19}$ is hydrogen and the other one is independently selected from alkylaminocarbonyl, hydroxyalkyl, alkyl, alkoxy and alkoxyalkoxy;
or one of $R^{18}$ and $R^{19}$ is hydroxyalkyl and the other one is alkyl;
or $R^{18}$ and $R^{19}$ are both hydrogen at the same time, provided that $R^4$ is alkoxycarbonyl or $R^5$ is alkyl; and
$R^{20}$ is alkyl;
or a pharmaceutically acceptable salt thereof.

The compound of formula (I) is particularly useful in the treatment or prophylaxis of e.g. pain, in particular chronic pain, atherosclerosis, regulation of bone mass, inflammation, ischemia, reperfusion injury, fibrosis including systemic fibrosis, liver fibrosis, lung fibrosis, kidney fibrosis and systemic sclerosis, chronic kidney diseases including kidney fibrosis, chronic allograft nephropathy, diabetic nephropathy, hypertensive nephropaty, lupus nephritis and glomerulonephropathy, heart diseases including angina pectoris, cardiomyopathy, heart failure and myocardial infarction, autoimmune diseases including rheumatoid arthritis and systemic lupus erythematosus, graft versus host diseases, burning, hypertrophic scars, keloids, gingivitis, liver cirrhosis, tumors, pyrexia or thermal injury.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in preclinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by down-regulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl, isopropyl and tert.-butyl, more particularly methyl, isopropyl and ter.-butyl.

The term "alkoxy", alone or in combination, signifies a group of the formula alkyl-O— in which the term "alkyl" has the previously given significance, such as methoxy, ethoxy, n-propoxy, isopropoxy (or isopropyloxy), n-butoxy, isobutoxy, sec.butoxy and tert.butoxy, particularly methoxy, ethoxy, isopropoxy and n-butoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. Particular halogens are fluorine, bromine and chlorine.

The term "haloalkyl", alone or in combination, denotes an alkyl group substituted with at least one halogen, particularly substituted with one to five halogens, particularly one to three halogens. A particular "haloalkyl" is trifluoromethyl.

The terms "hydroxyl" and "hydroxy", alone or in combination, signify the —OH group.

The term "carbonyl", alone or in combination, signifies the —C(O)— group.

The term "nitro", alone or in combination, signifies the —$NO_2$ group.

The term "amino", alone or in combination, signifies the primary amino group (—$NH_2$), the secondary amino group (—NH—), or the tertiary amino group (—N—).

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to the following:

A compound of formula (I) wherein $A^1$ is —$CH_2$—;

A compound of formula (I) wherein $R^1$ is -$A^2$-$C(O)$—$R^3$ and $R^2$ is hydrogen;

A compound of formula (I) wherein $A^3$ is —$CR^{18}R^{19}$— or —$NR^{20}$—;

A compound of formula (I) wherein:
one of $R^{18}$ and $R^{19}$ is hydrogen and the other one is independently selected from tert-butylaminocarbonyl, hydroxymethyl, isopropyl, methoxy, ethoxy, isopropoxy, n-butoxy and methoxyethoxy;
or one of $R^{18}$ and $R^{19}$ is hydroxymethyl and the other one is isopropyl;
or $R^{18}$ and $R^{19}$ are both hydrogen at the same time, provided that $R^4$ is methoxycarbonyl or $R^5$ is methyl;

A compound of formula (I) wherein one of $R^{18}$ and $R^{19}$ is hydrogen and the other one is methoxyethoxy or n-butoxy;

A compound of formula (I) wherein $R^{20}$ is methyl or isopropyl;

A compound of formula (I) wherein $R^6$ and $R^7$ are independently selected from hydrogen and methyl;

A compound of formula (I) wherein $R^6$ and $R^7$ are both hydrogen at the same time;

A compound of formula (I) wherein $R^6$ and $R^7$ are both methyl at the same time;

A compound of formula (I) wherein one of $R^6$ and $R^7$ is hydrogen and the other one is methyl;

A compound of formula (I) wherein $R^8$ and $R^9$ are independently selected from hydrogen and methyl;

A compound of formula (I) wherein $R^8$ and $R^9$ are both hydrogen at the same time; A compound of formula (I) wherein $R^8$ and $R^9$ are both methyl at the same time;

A compound of formula (I) wherein one of $R^8$ and $R^9$ is hydrogen and the other one is methyl;

A compound of formula (I) wherein $R^{10}$ is hydrogen, alkyl or alkoxy, and $R^{11}$, $R^{12}$ and $R^{13}$ are independently selected from hydrogen, alkyl, nitro, fluoro, chloro, haloalkyl and alkoxy, provided that $R^{10}$, $R^{11}$, $R^{12}$ and $R^{13}$ are not all hydrogen at the same time;

A compound of formula (I) wherein $R^{10}$ is hydrogen, methyl or methoxy, and $R^{11}$, $R^{12}$ and $R^{13}$ are independently selected from hydrogen, methyl, nitro, fluoro, chloro, trifluoromethyl and methoxy, provided that $R^{10}$, $R^{11}$, $R^{12}$ and $R^{13}$ are not all hydrogen at the same time;

A compound of formula (I) wherein $R^{11}$ is hydrogen, nitro, halogen, alkyl or haloalkyl, and $R^{10}$, $R^{12}$ and $R^{13}$ are independently selected from hydrogen, alkyl, nitro, fluoro, chloro, haloalkyl and alkoxy, provided that $R^{10}$, $R^{11}$, $R^{12}$ and $R^{13}$ are not all hydrogen at the same time;

A compound of formula (I) wherein $R^{11}$ is hydrogen, nitro, fluoro, methyl or trifluoromethyl, and $R^{10}$, $R^{12}$ and $R^{13}$ are independently selected from hydrogen, methyl, nitro, fluoro, chloro and methoxy, provided that $R^{10}$, $R^{11}$, $R^{12}$ and $R^{13}$ are not all hydrogen at the same time;

A compound of formula (I) wherein $R^{12}$ is hydrogen, halogen, nitro or alkyl, and $R^{10}$, $R^{11}$ and $R^{13}$ are independently selected from hydrogen, alkyl, nitro, fluoro, chloro, haloalkyl and alkoxy, provided that $R^{10}$, $R^{11}$, $R^{12}$ and $R^{13}$ are not all hydrogen at the same time;

A compound of formula (I) wherein $R^{12}$ is hydrogen, fluoro, nitro or methyl, and $R^{10}$, $R^{11}$ and $R^{13}$ are independently selected from hydrogen, methyl, nitro, fluoro, chloro, trifluoromethyl and methoxy, provided that $R^{10}$, $R^{11}$, $R^{12}$ and $R^{13}$ are not all hydrogen at the same time;

A compound of formula (I) wherein $R^{13}$ is hydrogen, halogen, alkyl or alkoxy, and $R^{10}$, $R^{11}$ and $R^{12}$ are independently selected from hydrogen, alkyl, nitro, fluoro, chloro, haloalkyl and alkoxy, provided that $R^{10}$, $R^{11}$, $R^{12}$ and $R^{13}$ are not all hydrogen at the same time.

A compound of formula (I) wherein $R^{13}$ is hydrogen, fluoro, chloro, methyl or methoxy, and $R^{10}$, $R^{11}$ and $R^{12}$ are independently selected from hydrogen, methyl, nitro, fluoro, trifluoromethyl and methoxy, provided that $R^{10}$, $R^{11}$, $R^{12}$ and $R^{13}$ are not all hydrogen at the same time;

A compound of formula (I) wherein $R^{13}$ is methoxycarbonyl and $R^{10}$, $R^{11}$ and $R^{12}$ are all hydrogen at the same time;

A compound of formula (I) wherein $R^{14}$ and $R^{17}$ are independently selected from hydrogen and fluoro;

A compound of formula (I) wherein $R^{15}$ and $R^{16}$ are independently selected from hydrogen, fluoro, chloro and morpholinyl;

A compound of formula (I) wherein $R^3$ is (A);
A compound of formula (I) wherein $R^3$ is (B);
A compound of formula (I) wherein $R^3$ is (C);

The invention further relates to a compound selected from
1-(Adamantane-1-carbonyl)-2,3-dihydro-1H-quinolin-4-one;
1-(Adamantane-1-carbonyl)-1,2,3,4-tetrahydro-quinoline-4-carboxylic acid tert-butylamide;
1-(Adamantane-1-carbonyl)-1,2,3,4-tetrahydro-quinoline-3-carboxylic acid methyl ester;

Adamantan-1-yl-(4-hydroxymethyl-4-isopropyl-3,4-dihydro-2H-quinolin-1-yl)-methanone;
Adamantan-1-yl-(8-methyl-3,4-dihydro-2H-quinolin-1-yl)-methanone;
Adamantan-1-yl-(4-ethoxy-3,4-dihydro-2H-quinolin-1-yl)-methanone;
Adamantan-1-yl-(6-nitro-2,3-dihydro-indol-1-yl)-methanone;
Adamantan-1-yl-(5-nitro-2,3-dihydro-indol-1-yl)-methanone;
Adamantan-1-yl-(4,6-difluoro-2,3-dihydro-indol-1-yl)-methanone;
Adamantan-1-yl-(6-trifluoromethyl-2,3-dihydro-indol-1-yl)-methanone;
Adamantan-1-yl-(5-fluoro-2,3-dihydro-indol-1-yl)-methanone;
Adamantan-1-yl-(4-chloro-2,3-dihydro-pyrrolo[3,2-c]pyridin-1-yl)-methanone;
Adamantan-1-yl-(1,3-dihydro-isoindol-2-yl)-methanone;
Adamantan-1-yl-(7-methoxy-2,3-dihydro-indol-1-yl)-methanone;
Adamantan-1-yl-(3,3-dimethyl-2,3-dihydro-indol-1-yl)-methanone;
1-(Adamantane-1-carbonyl)-2,3-dihydro-1H-indole-4-carboxylic acid methyl ester;
Adamantan-1-yl-(2,3-dimethyl-2,3-dihydro-indol-1-yl)-methanone;
Adamantan-1-yl-(5-methyl-2,3-dihydro-indol-1-yl)-methanone;
Adamantan-1-yl-(6-methyl-2,3-dihydro-indol-1-yl)-methanone;
Adamantan-1-yl-(7-methyl-2,3-dihydro-indol-1-yl)-methanone;
Adamantan-1-yl-(4-methoxy-2,3-dihydro-indol-1-yl)-methanone;
Adamantan-1-yl-(4-methyl-2,3-dihydro-indol-1-yl)-methanone;
Adamantan-1-yl-(4-methyl-3,4-dihydro-2H-quinoxalin-1-yl)-methanone;
Adamantan-1-yl-(4-isopropyl-3,4-dihydro-2H-quinoxalin-1-yl)-methanone;
Adamantan-1-yl-[4-(2-methoxy-ethoxy)-3,4-dihydro-2H-quinolin-1-yl]-methanone;
Adamantan-1-yl-(4-butoxy-3,4-dihydro-2H-quinolin-1-yl)-methanone;
Adamantan-1-yl-(4-isopropoxy-3,4-dihydro-2H-quinolin-1-yl)-methanone;
Adamantan-1-yl-(4-methoxy-3,4-dihydro-2H-quinolin-1-yl)-methanone;
Adamantan-2-yl-(2,3-dihydro-indol-1-yl)-methanone;
Adamantan-1-yl-(5,6-difluoro-2,3-dihydro-indol-1-yl)-methanone;
5-(2,3-Dihydro-indole-1-carbonyl)-adamantan-2-one;
(2,3-Dihydro-indol-1-yl)-(3-hydroxy-adamantan-1-yl)-methanone;
1,3-Dihydro-isoindole-2-carboxylic acid adamantan-1-ylamide;
Adamantan-1-yl-(5-chloro-6-morpholin-4-yl-1,3-dihydro-isoindol-2-yl)-methanone;
Adamantan-1-yl-(4-fluoro-1,3-dihydro-isoindol-2-yl)-methanone; and
Adamantan-1-yl-(5-fluoro-1,3-dihydro-isoindol-2-yl)-methanone.

The invention further relates to a compound selected from
Adamantan-1-yl-(5-fluoro-2,3-dihydro-indol-1-yl)-methanone;
Adamantan-1-yl-(4-isopropyl-3,4-dihydro-2H-quinoxalin-1-yl)-methanone;
Adamantan-1-yl-(4-butoxy-3,4-dihydro-2H-quinolin-1-yl)-methanone; and
Adamantan-2-yl-(2,3-dihydro-indol-1-yl)-methanone.

The invention further relates to a compound of formula (I) as defined above, for the treatment or the prevention of diseases which are modulated by the Cannabinoid Receptor 2.

The invention thus also relates to:

A compound of formula (I) for use as a medicament;

A pharmaceutical composition comprising a of formula (I);

The use of a compound of formula (I) for the treatment or the prevention of pain, in particular chronic pain, atherosclerosis, regulation of bone mass, inflammation, ischemia, reperfusion injury, fibrosis including systemic fibrosis, liver fibrosis, lung fibrosis, kidney fibrosis and systemic sclerosis, chronic kidney diseases including kidney fibrosis, chronic allograft nephropathy, diabetic nephropathy, hypertensive nephropaty, lupus nephritis and glomerulonephropathy, heart diseases including angina pectoris, cardiomyopathy, heart failure and myocardial infarction, autoimmune diseases including rheumatoid arthritis and systemic lupus erythematosus, graft versus host diseases, burning, hypertrophic scars, keloids, gingivitis, liver cirrhosis, tumors, pyrexia or thermal injury;

The use of a compound of formula (I) for the preparation of a medicament for the treatment or the prevention of pain, in particular chronic pain, atherosclerosis, regulation of bone mass, inflammation, ischemia, reperfusion injury, fibrosis including systemic fibrosis, liver fibrosis, lung fibrosis, kidney fibrosis and systemic sclerosis, chronic kidney diseases including kidney fibrosis, chronic allograft nephropathy, diabetic nephropathy, hypertensive nephropaty, lupus nephritis and glomerulonephropathy, heart diseases including angina pectoris, cardiomyopathy, heart failure and myocardial infarction, autoimmune diseases including rheumatoid arthritis and systemic lupus erythematosus, graft versus host diseases, burning, hypertrophic scars, keloids, gingivitis, liver cirrhosis, tumors, pyrexia or thermal injury;

A compound of formula (I) for use in the treatment or the prevention of pain, in particular chronic pain, atherosclerosis, regulation of bone mass, inflammation, ischemia, reperfusion injury, fibrosis including systemic fibrosis, liver fibrosis, lung fibrosis, kidney fibrosis and systemic sclerosis, chronic kidney diseases including kidney fibrosis, chronic allograft nephropathy, diabetic nephropathy, hypertensive nephropaty, lupus nephritis and glomerulonephropathy, heart diseases including angina pectoris, cardiomyopathy, heart failure and myocardial infarction, autoimmune diseases including rheumatoid arthritis and systemic lupus erythematosus, graft versus host diseases, burning, hypertrophic scars, keloids, gingivitis, liver cirrhosis, tumors, pyrexia or thermal injury; and A method for the treatment or the prevention of pain, in particular chronic pain, atherosclerosis, regulation of bone mass, inflammation, ischemia, reperfusion injury, fibrosis including systemic fibrosis, liver fibrosis, lung fibrosis, kidney fibrosis and systemic sclerosis, chronic kidney diseases including kidney fibrosis, chronic allograft nephropathy, diabetic nephropathy, hypertensive nephropaty, lupus nephritis and glomerulonephropathy, heart diseases including angina pectoris, cardiomyopathy, heart failure and myocardial infarction, autoimmune diseases including rheumatoid arthritis and systemic lupus erythematosus, graft versus host diseases, burning, hypertrophic scars, keloids, gingivitis, liver cirrhosis, tumors, pyrexia or thermal injury, which method comprises administering an effective amount of a compound of formula (I) to a patient in need thereof.

The compounds of the present invention are particularly useful in the treatment or the prevention of chronic kidney diseases, in particular kidney fibrosis, chronic allograft nephropathy, diabetic nephropathy, hypertensive nephropaty, lupus nephritis and glomerulonephropathy.

The compounds of the present invention are particularly useful in the treatment of pain.

The invention also relates to a compound selected from
Adamantan-1-yl-(3,4-dihydro-1H-isoquinolin-2-yl)-methanone;
Adamantan-1-yl-(3,4-dihydro-2H-quinolin-1-yl)-methanone;
Adamantan-1-yl-(2,3-dihydro-benzo[1,4]oxazin-4-yl)-methanone;
Adamantan-1-yl-(4-hydroxy-3,4-dihydro-2H-quinolin-1-yl)-methanone;
Adamantan-1-yl-(2-methyl-2,3-dihydro-indol-1-yl)-methanone;
Adamantan-1-yl-(2,3-dihydro-indol-1-yl)-methanone;
Adamantan-1-yl-(5-bromo-2,3-dihydro-indol-1-yl)-methanone;
1-(Adamantane-1-carbonyl)-2,3-dihydro-1H-indole-5-carboxylic acid methyl ester; and
2,3-Dihydro-indole-1-carboxylic acid adamantan-1-ylamide;
for the treatment or the prevention of a disease modulated by CB2.

The invention thus also relates to a compound selected from
Adamantan-1-yl-(3,4-dihydro-1H-isoquinolin-2-yl)-methanone;
Adamantan-1-yl-(3,4-dihydro-2H-quinolin-1-yl)-methanone;
Adamantan-1-yl-(2,3-dihydro-benzo[1,4]oxazin-4-yl)-methanone;
Adamantan-1-yl-(4-hydroxy-3,4-dihydro-2H-quinolin-1-yl)-methanone;
Adamantan-1-yl-(2-methyl-2,3-dihydro-indol-1-yl)-methanone;
Adamantan-1-yl-(2,3-dihydro-indol-1-yl)-methanone;
Adamantan-1-yl-(5-bromo-2,3-dihydro-indol-1-yl)-methanone;
1-(Adamantane-1-carbonyl)-2,3-dihydro-1H-indole-5-carboxylic acid methyl ester; and
2,3-Dihydro-indole-1-carboxylic acid adamantan-1-ylamide;
for the treatment or the prevention of pain, in particular chronic pain, atherosclerosis, regulation of bone mass, inflammation, ischemia, reperfusion injury, fibrosis including systemic fibrosis, liver fibrosis, lung fibrosis, kidney fibrosis and systemic sclerosis, chronic kidney diseases including kidney fibrosis, chronic allograft nephropathy, diabetic nephropathy, hypertensive nephropaty, lupus nephritis and glomerulonephropathy, heart diseases including angina pectoris, cardiomyopathy, heart failure and myocardial infarction, autoimmune diseases including rheumatoid arthritis and systemic lupus erythematosus, graft versus host diseases, burning, hypertrophic scars, keloids, gingivitis, liver cirrhosis, tumors, pyrexia or thermal injury.

The invention also relates to a compound selected from
Adamantan-1-yl-(3,4-dihydro-1H-isoquinolin-2-yl)-methanone;
Adamantan-1-yl-(3,4-dihydro-2H-quinolin-1-yl)-methanone;
Adamantan-1-yl-(2,3-dihydro-benzo[1,4]oxazin-4-yl)-methanone;
Adamantan-1-yl-(4-hydroxy-3,4-dihydro-2H-quinolin-1-yl)-methanone;
Adamantan-1-yl-(2-methyl-2,3-dihydro-indol-1-yl)-methanone;
Adamantan-1-yl-(2,3-dihydro-indol-1-yl)-methanone;
Adamantan-1-yl-(5-bromo-2,3-dihydro-indol-1-yl)-methanone;
1-(Adamantane-1-carbonyl)-2,3-dihydro-1H-indole-5-carboxylic acid methyl ester; and
2,3-Dihydro-indole-1-carboxylic acid adamantan-1-ylamide;
for the treatment or the prevention of pain.

The compounds defined above may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of the invention is formulated in an acetate buffer, at pH 5. In another embodiment, the compounds of the invention are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity, the sequence of reaction steps can be freely altered. Starting materials are either commercially available or can be prepared by methods analogous to the methods given below, by methods described in references cited in the description or in the examples, or by methods known in the art.

Scheme 1

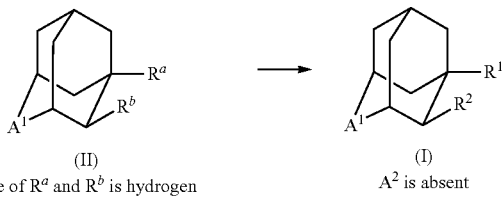

(II)
One of $R^a$ and $R^b$ is hydrogen
and the other one is -COOH or COCl (I)
$A^2$ is absent Synthesis of the compound of formula (I) in case $A^2$ is absent can be carried out as follows. Substituted and unsubstituted 1- and 2-adamantane carboxylic acids or acid chlorides (II) are either commercially available or can be synthesised according to methods known in the art. The respective acid or acid chlorides (II) can be reacted with suitable amines in the presence of a base like NEt₃ or DIPEA (diisopropylethylamine) to yield final adamantyl derivatives (I).

Scheme 2

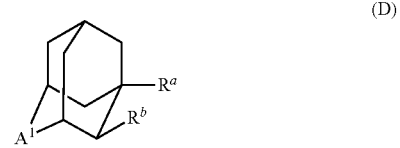

(III)
One of $R^a$ and $R^b$ is hydrogen
and the other one is -N=C=O (I)
$A^2$ is -NH- Synthesis of the compound of formula (I) in case $A^2$ is —NH— can be carried out as follows. Substituted and unsubstituted 1- and 2-adamantane isocyanates (III) are either commercially available or can be synthesised according to methods known in the art. The respective derivatives (III) can be reacted with suitable amines in the presence of a base like NEt₃ or DIPEA to yield final adamantyl derivatives (I).

The invention therefore also relates to a process for the preparation of a compound of formula (I) as defined above comprising one of the following steps:

(a) The reaction of a compound of formula (D)

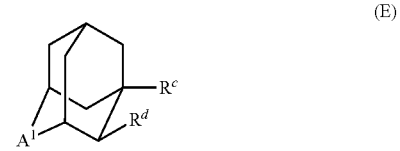

in the presence of R³—H and a base; or (b) The reaction of a compound of formula (E)

(E)

in the presence of R³—H and a base;
wherein
one of Ra and $R^b$ is hydrogen and the other one is —COOH or —COCl;
one of Rc and $R^d$ is hydrogen and the other one is —N=C=O;
and wherein $A^1$ and $R^3$ are as defined above.

A suitable base for the process of the invention can be for example NEt₃ or DIPEA.

The invention also relates to a compound of formula (I) prepared by a process according to the invention.

The invention will now be illustrated by the following examples which have no limiting character.

EXAMPLES

Example 1

Adamantan-1-yl-(3,4-dihydro-1H-isoquinolin-2-yl)-methanone

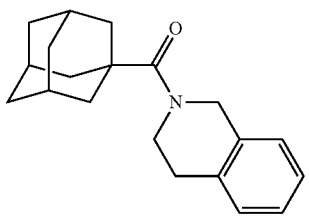 [SMILES: O=C(N1CCc2ccccc2C1)C12CC3CC(CC(C3)C1)C2]

A mixture of 20 mg (0.15 mmol) 1,2,3,4-tetrahydroisoquinoline, 32.8 mg (0.165 mmol) 1-adamatanecarbonyl chloride and 45.5 mg (0.45 mmol) NEt$_3$ in 2 mL DCM was shaken at room temperature overnight. The mixture was evaporated and subjected to column chromatography on reversed phase eluting with a gradient formed from acetonitrile, water and formic acid to yield after evaporation of the product containing fractions 30.1 mg (68%) of the title compound as white solid. MS(m/e): 296.3 (MH$^+$).

Example 2

Adamantan-1-yl-(3,4-dihydro-2H-quinolin-1-yl)-methanone

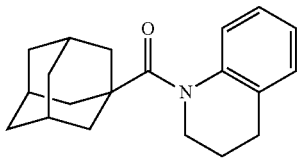 [SMILES: O=C(N1CCCc2ccccc21)C12CC3CC(CC(C3)C1)C2]

A mixture of 24.5 mg (0.18 mmol) 1,2,3,4-tetrahydroquinoline, 37.3 mg (0.188 mmol) 1-adamatanecarbonyl chloride and 44.4 mg (0.34 mmol) DIPEA in 1 mL DCM was shaken at room temperature for 4 h. The mixture was evaporated, dissolved in DMF and subjected to column chromatography on reversed phase eluting with a gradient formed from acetonitrile, water and formic acid to yield after evaporation of the product containing fractions 34.9 mg (64%) of the title compound as white solid. MS(m/e): 296.3 (MH$^+$).

Example 3

1-(Adamantane-1-carbonyl)-2,3-dihydro-1H-quinolin-4-one

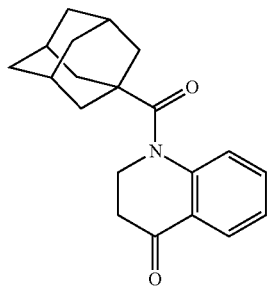 [SMILES: O=C1CCN(C(=O)C23CC4CC(CC(C4)C2)C3)c2ccccc21]

A mixture of 25.2 mg (0.17 mmol) 2,3-dihydroquinolin-4(1H)-one and 52.9 mg (0.26 mmol) adamatanecarbonyl chloride in 0.9 mL dioxane and 0.041 mL pyridine was shaken at 110° C. for 16 h. The mixture was evaporated, dissolved in DMF and subjected to column chromatography on reversed phase eluting with a gradient formed from acetonitrile, water and formic acid to yield after evaporation of the product containing fractions 11.5 mg (22%) of the title compound as white solid. MS(m/e): 310.4 (MH$^+$).

Example 4

1-(Adamantane-1-carbonyl)-1,2,3,4-tetrahydroquinoline-4-carboxylic acid tert-butylamide

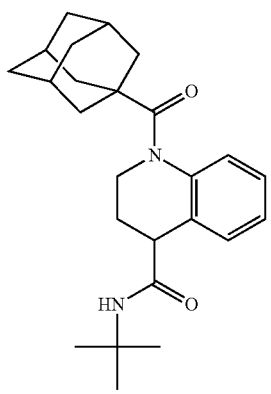 [SMILES: CC(C)(C)NC(=O)C1CCN(C(=O)C23CC4CC(CC(C4)C2)C3)c2ccccc21]

In analogy to the procedure described for the synthesis of adamantan-1-yl-(3,4-dihydro-2H-quinolin-1-yl)-methanone (example 2) the title compound was prepared from N-tert-butyl-1,2,3,4-tetrahydroquinoline-4-carboxamide and adamatanecarbonyl chloride as white solid. MS(m/e): 395.3 (MH$^+$).

Example 5

1-(Adamantane-1-carbonyl)-1,2,3,4-tetrahydroquinoline-3-carboxylic acid methyl ester

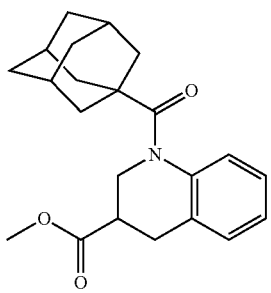 [SMILES: COC(=O)C1Cc2ccccc2N(C(=O)C23CC4CC(CC(C4)C2)C3)C1]

In analogy to the procedure described for the synthesis of adamantan-1-yl-(3,4-dihydro-2H-quinolin-1-yl)-methanone (example 2) the title compound was prepared from methyl 1,2,3,4-tetrahydroquinoline-3-carboxylate and adamatanecarbonyl chloride as colourless viscous oil. MS(m/e): 354.4 (MH$^+$).

Example 6

Adamantan-1-yl-(4-hydroxymethyl-4-isopropyl-3,4-dihydro-2H-quinolin-1-yl)-methanone

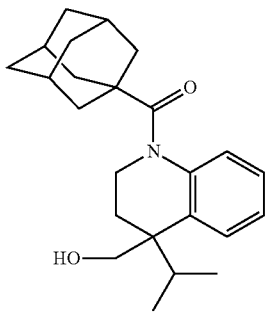 [SMILES: CC(C)C1(CO)CCN(C(=O)C23CC4CC(CC(C4)C2)C3)c2ccccc21]

In analogy to the procedure described for the synthesis of adamantan-1-yl-(3,4-dihydro-2H-quinolin-1-yl)-methanone (example 2) the title compound was prepared from (4-isopropyl-1,2,3,4-tetrahydroquinolin-4-yl)methanol hydrochloride and adamatanecarbonyl chloride as white solid. MS(m/e): 368.3 (MH$^+$).

Example 7

Adamantan-1-yl-(2,3-dihydro-benzo[1,4]oxazin-4-yl)-methanone

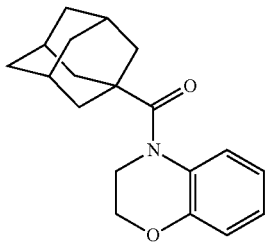 [SMILES: O=C(N1CCOc2ccccc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 3,4-dihydro-2H-benzo[b][1,4]oxazine and adamatanecarbonyl chloride as yellow solid. MS(m/e): 298.4 (MH$^+$).

Example 8

Adamantan-1-yl-(8-methyl-3,4-dihydro-2H-quinolin-1-yl)-methanone

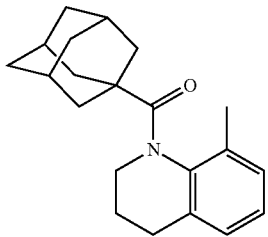 [SMILES: Cc1cccc2c1N(C(=O)C13CC4CC(CC(C4)C1)C3)CCC2]

In analogy to the procedure described for the synthesis of adamantan-1-yl-(3,4-dihydro-1H-isoquinolin-2-yl)-methanone (example 1) the title compound was prepared from 8-methyl-1,2,3,4-tetrahydroquinoline and adamatanecarbonyl chloride as white solid. MS(m/e): 310.4 (MH$^+$).

Example 9

Adamantan-1-yl-(4-hydroxy-3,4-dihydro-2H-quinolin-1-yl)-methanone

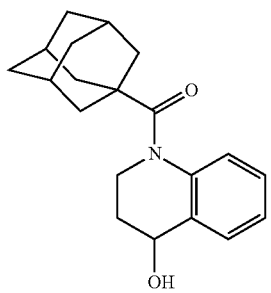 [SMILES: O=C(N1CCC(O)c2ccccc21)C12CC3CC(CC(C3)C1)C2]

A mixture of 0.6 g (1.94 mmol) 1-(Adamantane-1-carbonyl)-2,3-dihydro-1H-quinolin-4-one and 0.11 g (2.91 mmol) NaBH$_4$ in 20 mL methanol was stirred at room temperature. The mixture was evaporated, taken up on isolute and subjected to column chromatography on silica eluting with a gradient formed from heptane and TBME to yield after evaporation of the product containing fractions 0.557 g (92%) as white solid. MS(m/e): 312.4 (MH$^+$).

Example 10

Adamantan-1-yl-(2-methyl-2,3-dihydro-indol-1-yl)-methanone

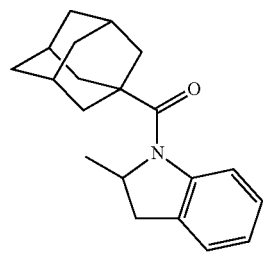 [SMILES: CC1Cc2ccccc2N1C(=O)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 2-methylindoline and adamatanecarbonyl chloride as white solid. MS(m/e): 296.4 (MH$^+$).

Example 11

Adamantan-1-yl-(2,3-dihydro-indol-1-yl)-methanone

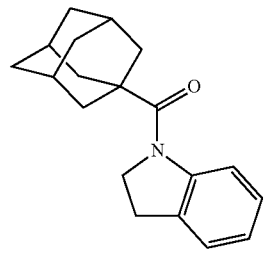 [SMILES: O=C(N1CCc2ccccc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from indoline and adamatanecarbonyl chloride as white solid. MS(m/e): 282.4 (MH⁺).

Example 12

Adamantan-1-yl-(4-ethoxy-3,4-dihydro-2H-quinolin-1-yl)-methanone

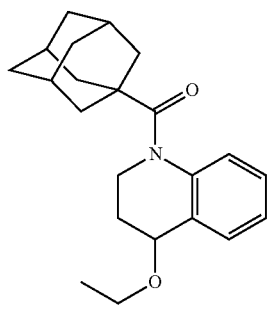 [SMILES: CCOC1CCN(C(=O)C23CC4CC(CC(C4)C2)C3)c2ccccc21]

A mixture of 0.1 g (0.32 mmol) adamantan-1-yl-(4-hydroxy-3,4-dihydro-2H-quinolin-1-yl)-methanone and 35 mg (55% in oil, 0.8 mmol) NaH in 5 mL THF at 0° C. was treated with 0.15 g (0.99 mmol) iododethane and allowed to stir to room temperature and subsequently heated to 50° C. overnight. The mixture was diluted with water and extracted with ethyl acetate. The combined organic phases were dried with MgSO₄, filtered and evaporated. The residue was subjected to column chromatography on reversed phase eluting with a gradient formed from acetonitrile, water and formic acid to yield after evaporation of the product containing fractions 24.5 mg (22%) of the title compound as colourless solid. MS(m/e): 340.3 (MH⁺).

Example 13

Adamantan-1-yl-(6-nitro-2,3-dihydro-indol-1-yl)-methanone

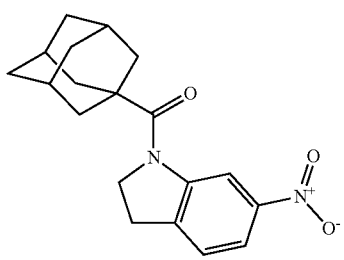 [SMILES: O=C(N1CCc2ccc([N+](=O)[O-])cc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 6-nitroindoline and adamatanecarbonyl chloride as white solid. MS(m/e): 327.3 (MH⁺).

Example 14

Adamantan-1-yl-(5-nitro-2,3-dihydro-indol-1-yl)-methanone

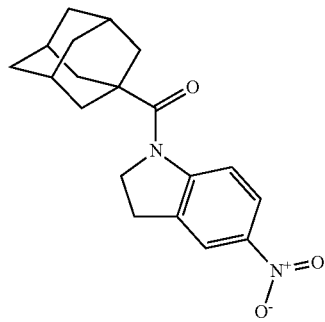 [SMILES: O=C(N1CCc2cc([N+](=O)[O-])ccc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 5-nitroindoline and adamatanecarbonyl chloride as white solid. MS(m/e): 327.3 (MH⁺).

Example 15

Adamantan-1-yl-(5-bromo-2,3-dihydro-indol-1-yl)-methanone

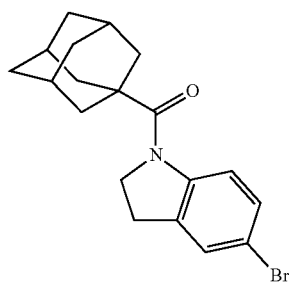 [SMILES: O=C(N1CCc2cc(Br)ccc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 5-nitroindoline and adamatanecarbonyl chloride as white solid. MS(m/e): 327.3 (MH⁺).

Example 16

Adamantan-1-yl-(4,6-difluoro-2,3-dihydro-indol-1-yl)-methanone

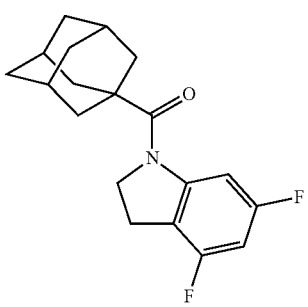 [SMILES: O=C(N1CCc2c(F)cc(F)cc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 4,6-difluoroindoline and adamatanecarbonyl chloride as white solid. MS(m/e): 318.2 (MH$^+$).

Example 17

Adamantan-1-yl-(6-trifluoromethyl-2,3-dihydro-indol-1-yl)-methanone

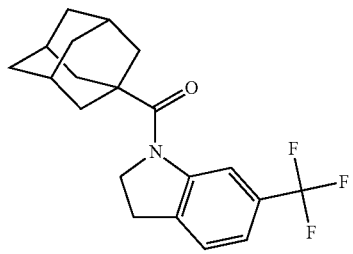 [SMILES: O=C(N1CCc2ccc(C(F)(F)F)cc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 6-(trifluoromethyl)indoline and adamatanecarbonyl chloride as white solid. MS(m/e): 350.3 (MH$^+$).

Example 18

Adamantan-1-yl-(5-fluoro-2,3-dihydro-indol-1-yl)-methanone

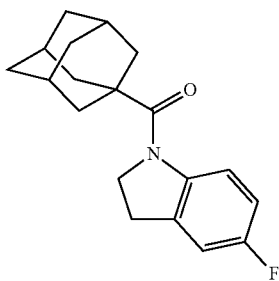 [SMILES: O=C(N1CCc2cc(F)ccc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 5-fluoroindoline and adamatanecarbonyl chloride as white solid. MS(m/e): 300.3 (MH$^+$).

Example 19

1-(Adamantane-1-carbonyl)-2,3-dihydro-1H-indole-5-carboxylic acid methyl ester

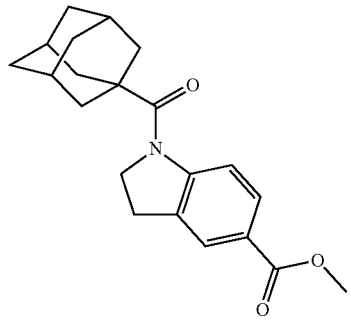 [SMILES: COC(=O)c1ccc2c(c1)CCN2C(=O)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from methyl indoline-5-carboxylate and adamatanecarbonyl chloride as white solid. MS(m/e): 340.2 (MH$^+$).

Example 20

Adamantan-1-yl-(4-chloro-2,3-dihydro-pyrrolo[3,2-c]pyridin-1-yl)-methanone

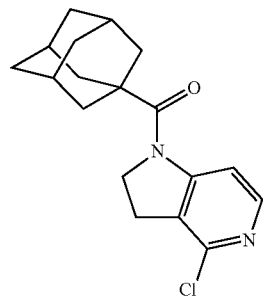 [SMILES: O=C(N1CCc2c1ccnc2Cl)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 4-chloro-2,3-dihydro-1H-pyrrolo[3,2-c]pyridine and adamatanecarbonyl chloride as white solid. MS(m/e): 317.2 (MH$^+$).

Example 21

Adamantan-1-yl-(1,3-dihydro-isoindol-2-yl)-methanone

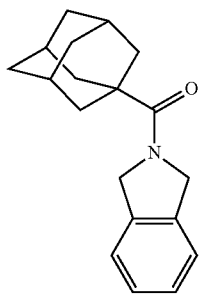 [SMILES: O=C(N1Cc2ccccc2C1)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from isoindoline and adamatanecarbonyl chloride as white solid. MS(m/e): 282.4 (MH⁺).

Example 22

Adamantan-1-yl-(7-methoxy-2,3-dihydro-indol-1-yl)-methanone

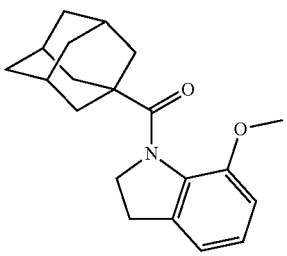 [SMILES: COc1cccc2c1N(C(=O)C13CC4CC(CC(C4)C1)C3)CC2]

In analogy to the procedure described for the synthesis of adamantan-1-yl-(3,4-dihydro-1H-isoquinolin-2-yl)-methanone (example 1) the title compound was prepared from 7-methoxyindoline and adamatanecarbonyl chloride as white solid. MS(m/e): 312.4 (MH⁺).

Example 23

Adamantan-1-yl-(3,3-dimethyl-2,3-dihydro-indol-1-yl)-methanone

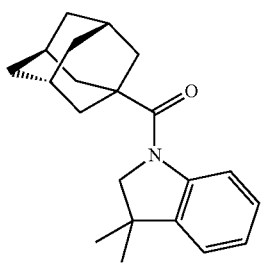 [SMILES: CC1(C)CN(C(=O)C23C[C@H]4C[C@@H](C2)C[C@@H](C3)C4)c2ccccc21]

In analogy to the procedure described for the synthesis of adamantan-1-yl-(3,4-dihydro-1H-isoquinolin-2-yl)-methanone (example 1) the title compound was prepared from 3,3-dimethylindoline and adamatanecarbonyl chloride. MS(m/e): 310.4 (MH⁺).

Example 24

1-(Adamantane-1-carbonyl)-2,3-dihydro-1H-indole-4-carboxylic acid methyl ester

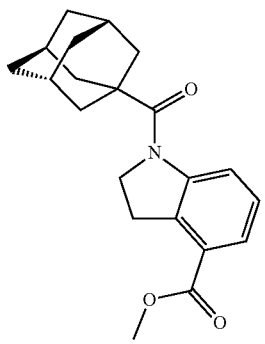 [SMILES: COC(=O)c1cccc2c1CCN2C(=O)C12C[C@H]3C[C@@H](C1)C[C@@H](C2)C3]

In analogy to the procedure described for the synthesis of adamantan-1-yl-(3,4-dihydro-1H-isoquinolin-2-yl)-methanone (example 1) the title compound was prepared from methyl indoline-4-carboxylate and adamatanecarbonyl chloride. MS(m/e): 340.2 (MH⁺).

Example 25

Adamantan-1-yl-(2,3-dimethyl-2,3-dihydro-indol-1-yl)-methanone

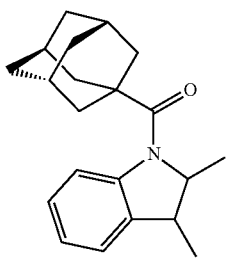 [SMILES: CC1c2ccccc2N(C(=O)C23C[C@H]4C[C@@H](C2)C[C@@H](C3)C4)C1C]

In analogy to the procedure described for the synthesis of adamantan-1-yl-(3,4-dihydro-1H-isoquinolin-2-yl)-methanone (example 1) the title compound was prepared from 2,3-dimethylindoline and adamatanecarbonyl chloride. MS(m/e): 310.4 (MH⁺).

Example 26

Adamantan-1-yl-(5-methyl-2,3-dihydro-indol-1-yl)-methanone

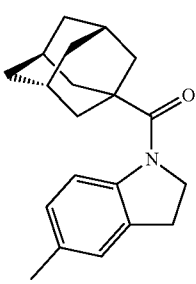 [SMILES: Cc1ccc2c(c1)CCN2C(=O)C12C[C@H]3C[C@@H](C1)C[C@@H](C2)C3]

In analogy to the procedure described for the synthesis of adamantan-1-yl-(3,4-dihydro-1H-isoquinolin-2-yl)-methanone (example 1) the title compound was prepared from 5-methylindoline and adamatanecarbonyl chloride. MS(m/e): 296.4 (MH+).

Example 27

Adamantan-1-yl-(6-methyl-2,3-dihydro-indol-1-yl)-methanone

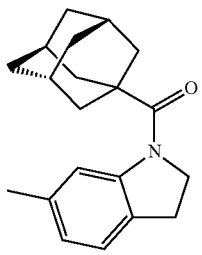 [SMILES: Cc1ccc2c(c1)N(C(=O)C13C[C@H]4C[C@@H](C1)C[C@@H](C3)C4)CC2]

In analogy to the procedure described for the synthesis of adamantan-1-yl-(3,4-dihydro-1H-isoquinolin-2-yl)-methanone (example 1) the title compound was prepared from 6-methylindoline and adamatanecarbonyl chloride. MS(m/e): 296.4 (MH+).

Example 28

Adamantan-1-yl-(7-methyl-2,3-dihydro-indol-1-yl)-methanone

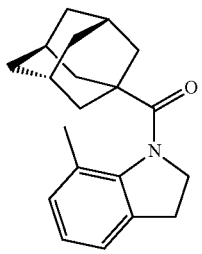 [SMILES: Cc1cccc2c1N(C(=O)C13C[C@H]4C[C@@H](C1)C[C@@H](C3)C4)CC2]

In analogy to the procedure described for the synthesis of adamantan-1-yl-(3,4-dihydro-1H-isoquinolin-2-yl)-methanone (example 1) the title compound was prepared from 7-methylindoline and adamatanecarbonyl chloride. MS(m/e): 296.4 (MH+).

Example 29

Adamantan-1-yl-(4-methoxy-2,3-dihydro-indol-1-yl)-methanone

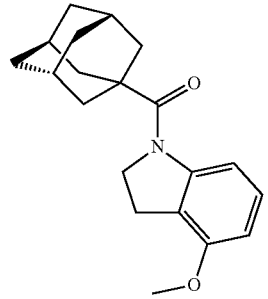 [SMILES: COc1cccc2c1CCN2C(=O)C12C[C@H]3C[C@@H](C1)C[C@@H](C2)C3]

In analogy to the procedure described for the synthesis of adamantan-1-yl-(3,4-dihydro-1H-isoquinolin-2-yl)-methanone (example 1) the title compound was prepared from 4-methoxyindoline and adamatanecarbonyl chloride. MS(m/e): 312.4 (MH+).

Example 30

Adamantan-1-yl-(4-methyl-2,3-dihydro-indol-1-yl)-methanone

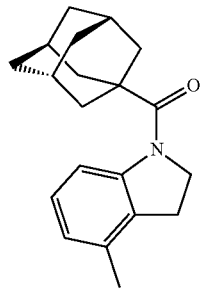 [SMILES: Cc1cccc2c1CCN2C(=O)C12C[C@H]3C[C@@H](C1)C[C@@H](C2)C3]

In analogy to the procedure described for the synthesis of adamantan-1-yl-(3,4-dihydro-1H-isoquinolin-2-yl)-methanone (example 1) the title compound was prepared from 4-methylindoline and adamatanecarbonyl chloride. MS(m/e): 296.4 (MH+).

Example 31

Adamantan-1-yl-(4-methyl-3,4-dihydro-2H-quinoxalin-1-yl)-methanone

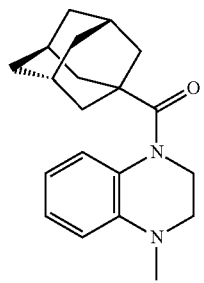 [SMILES: CN1CCN(C(=O)C23C[C@H]4C[C@@H](C2)C[C@@H](C3)C4)c2ccccc21]

In analogy to the procedure described for the synthesis of adamantan-1-yl-(3,4-dihydro-1H-isoquinolin-2-yl)-methanone (example 1) the title compound was prepared from 1-methyl-1,2,3,4-tetrahydroquinoxaline and adamatanecarbonyl chloride. MS(m/e): 311.4 (MH$^+$).

Example 32

Adamantan-1-yl-(4-isopropyl-3,4-dihydro-2H-quinoxalin-1-yl)-methanone

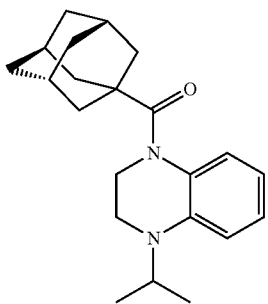 [SMILES: CC(C)N1CCN(C(=O)C23C[C@H]4C[C@@H](C2)C[C@@H](C3)C4)c2ccccc21]

In analogy to the procedure described for the synthesis of adamantan-1-yl-(3,4-dihydro-1H-isoquinolin-2-yl)-methanone (example 1) the title compound was prepared from 1-isopropyl-1,2,3,4-tetrahydroquinoxaline and adamatanecarbonyl chloride. MS(m/e): 339.4 (MH$^+$).

Example 33

Adamantan-1-yl-[4-(2-methoxy-ethoxy)-3,4-dihydro-2H-quinolin-1-yl]-methanone

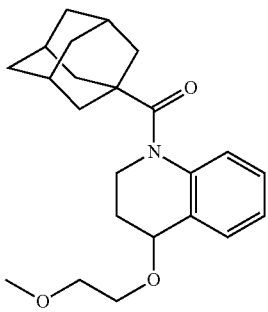 [SMILES: COCCOC1CCN(C(=O)C23CC4CC(CC(C4)C2)C3)c2ccccc21]

In analogy to the procedure described for the synthesis of adamantan-1-yl-(4-ethoxy-3,4-dihydro-2H-quinolin-1-yl)-methanone (example 12) the title compound was prepared from adamantan-1-yl-(4-hydroxy-3,4-dihydro-2H-quinolin-1-yl)-methanone and 1-bromo-2-methoxyethane in THF. MS(m/e): 370.3 (MH$^+$).

Example 34

Adamantan-1-yl-(4-butoxy-3,4-dihydro-2H-quinolin-1-yl)-methanone

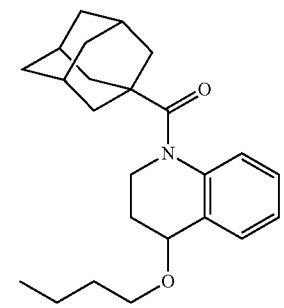 [SMILES: CCCCOC1CCN(C(=O)C23CC4CC(CC(C4)C2)C3)c2ccccc21]

In analogy to the procedure described for the synthesis of adamantan-1-yl-(4-ethoxy-3,4-dihydro-2H-quinolin-1-yl)-methanone (example 12) the title compound was prepared from adamantan-1-yl-(4-hydroxy-3,4-dihydro-2H-quinolin-1-yl)-methanone and 1-iodobutane as colourless solid. MS(m/e): 368.3 (MH$^+$).

Example 35

Adamantan-1-yl-(4-isopropoxy-3,4-dihydro-2H-quinolin-1-yl)-methanone

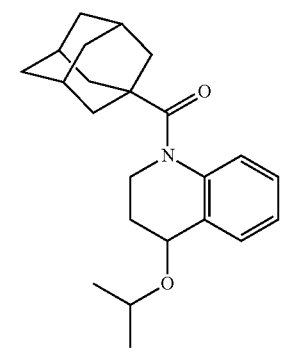 [SMILES: CC(C)OC1CCN(C(=O)C23CC4CC(CC(C4)C2)C3)c2ccccc21]

In analogy to the procedure described for the synthesis of adamantan-1-yl-(4-ethoxy-3,4-dihydro-2H-quinolin-1-yl)-methanone (example 12) the title compound was prepared from adamantan-1-yl-(4-hydroxy-3,4-dihydro-2H-quinolin-1-yl)-methanone and 2-iodopropane as colourless solid. MS(m/e): 354.4 (MH$^+$).

Example 36

Adamantan-1-yl-(4-methoxy-3,4-dihydro-2H-quinolin-1-yl)-methanone

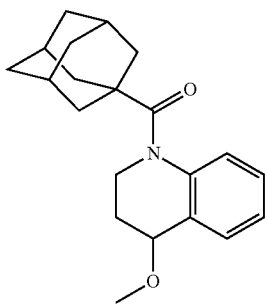 [SMILES: COC1CCN(C(=O)C23CC4CC(CC(C4)C2)C3)c2ccccc21]

In analogy to the procedure described for the synthesis of adamantan-1-yl-(4-ethoxy-3,4-dihydro-2H-quinolin-1-yl)-methanone (example 12) the title compound was prepared from adamantan-1-yl-(4-hydroxy-3,4-dihydro-2H-quinolin-1-yl)-methanone and methyliodide as light brown solid. MS(m/e): 326.3 (MH$^+$).

Example 37

Adamantan-2-yl-(2,3-dihydro-indol-1-yl)-methanone

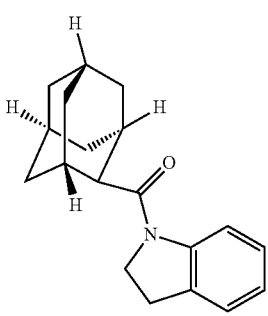 [SMILES: O=C(C1[C@H]2C[C@@H]3C[C@@H](C[C@H]1C3)C2)N1CCc2ccccc21]

A mixture of 24.2 mg (0.134 mmol) adamantane-2-carboxylic acid, 20 mg (0.168 mmol) indoline, 64.7 mg (0.2 mmol) TBTU and 43.4 mg (0.336 mmol) DIPEA in 1 mL DMF was stirred at room temperature overnight. Formic acid was added and the mixture was subjected to column chromatography on reversed phase eluting with a gradient formed from acetonitrile, water and NEt$_3$ to yield after evaporation of the product containing fractions 14.1 mg (30%) of the title compound. MS(m/e): 282.4 (MH$^+$).

Example 38

2,3-Dihydro-indole-1-carboxylic acid adamantan-1-ylamide

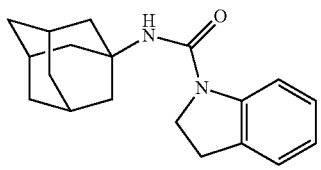 [SMILES: O=C(NC12CC3CC(CC(C3)C1)C2)N1CCc2ccccc21]

A mixture of 35.7 mg (0.2 mmol) 1-adamantyl isocyanate, 20 mg (0.168 mmol) indoline and 51 mg (0.5 mmol) NEt$_3$ in 2 mL DCM was shaken at room temperature overnight and evaporated to dryness. The residue was taken up in DMF and subjected to column chromatography on reversed phase eluting with a gradient formed from acetonitrile, water and formic acid to yield after evaporation of the product containing fractions 15.2 mg (30%) of the title compound as white solid. MS(m/e): 297.4 (MH$^+$).

Example 39

Adamantan-1-yl-(5,6-difluoro-2,3-dihydro-indol-1-yl)-methanone

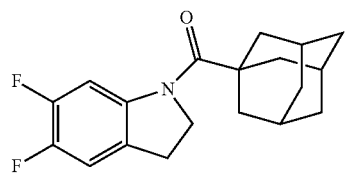 [SMILES: O=C(N1CCc2cc(F)c(F)cc21)C12CC3CC(CC(C3)C1)C2]

In analogy to the procedure described for the synthesis of adamantan-1-yl-(3,4-dihydro-1H-isoquinolin-2-yl)-methanone (example 1) the title compound was prepared from 5,6-difluoroindoline and adamatanecarbonyl chloride as light brown solid. MS(m/e): 318.3 (MH$^+$).

Example 40

5-(2,3-Dihydro-indole-1-carbonyl)-adamantan-2-one

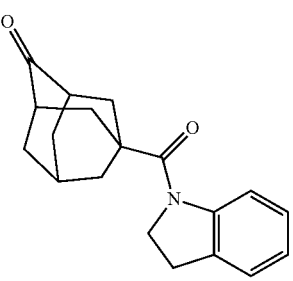 [SMILES: O=C1C2CC3CC4(C(=O)N5CCc6ccccc65)CC1C2(C3)C4]

In analogy to the procedure described for the synthesis of adamantan-2-yl-(2,3-dihydro-indol-1-yl)-methanone (example 37) the title compound was prepared from indoline and 4-keto-1-adamantanecarboxylic acid. MS(m/e): 296.2 (MH⁺).

Example 41

(2,3-Dihydro-indol-1-yl)-(3-hydroxy-adamantan-1-yl)-methanone

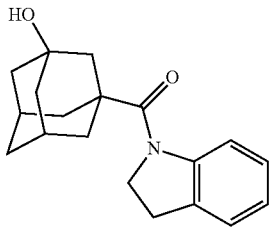 [SMILES: O=C(N1CCc2ccccc21)C12CC3CC(CC(O)(C3)C1)C2]

In analogy to the procedure described for the synthesis of adamantan-2-yl-(2,3-dihydro-indol-1-yl)-methanone (example 37) the title compound was prepared from indoline and 3-hydroxyadamantane-1-carboxylic acid. MS(m/e): 298.2 (MH⁺).

Example 42

1,3-Dihydro-isoindole-2-carboxylic acid adamantan-1-ylamide

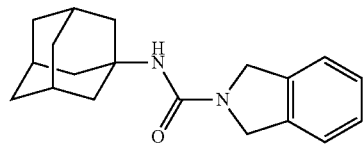 [SMILES: O=C(NC12CC3CC(CC(C3)C1)C2)N1Cc2ccccc2C1]

In analogy to the procedure described for the synthesis of 2,3-Dihydro-indole-1-carboxylic acid adamantan-1-ylamide (example 38) the title compound was prepared from isoindoline and 1-adamantyl isocyanate as light brown solid. MS(m/e): 297.3 (MH⁺).

Example 43

Adamantan-1-yl-(5-chloro-6-morpholin-4-yl-1,3-dihydro-isoindol-2-yl)-methanone

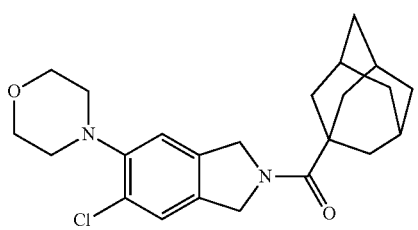 [SMILES: O=C(N1Cc2cc(Cl)c(N3CCOCC3)cc2C1)C12CC3CC4CC(C1)C4(C3)C2]

In analogy to the procedure described for the synthesis of adamantan-1-yl-(3,4-dihydro-1H-isoquinolin-2-yl)-methanone (example 1) the title compound was prepared from 4-(6-chloroisoindolin-5-yl)morpholine hydrochloride and adamatanecarbonyl chloride as white solid. MS(m/e): 401.4 (MH⁺).

Example 44

Adamantan-1-yl-(4-fluoro-1,3-dihydro-isoindol-2-yl)-methanone

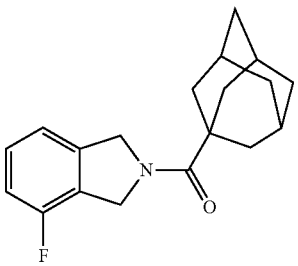 [SMILES: O=C(N1Cc2cccc(F)c2C1)C12CC3CC4CC(C1)C4(C3)C2]

In analogy to the procedure described for the synthesis of adamantan-1-yl-(3,4-dihydro-1H-isoquinolin-2-yl)-methanone (example 1) the title compound was prepared from 4-fluoroisoindoline hydrochloride and adamatanecarbonyl chloride as white solid. MS(m/e): 300.3 (MH⁺).

Example 45

Adamantan-1-yl-(5-fluoro-1,3-dihydro-isoindol-2-yl)-methanone

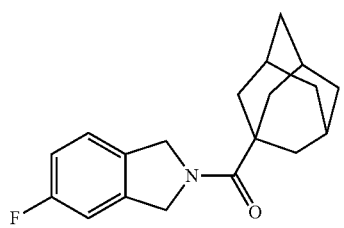 [SMILES: O=C(N1Cc2ccc(F)cc2C1)C12CC3CC4CC(C1)C4(C3)C2]

In analogy to the procedure described for the synthesis of adamantan-1-yl-(3,4-dihydro-1H-isoquinolin-2-yl)-methanone (example 1) the title compound was prepared from 5-fluoroisoindoline hydrochloride and adamatanecarbonyl chloride as white solid. MS(m/e): 300.2 (MH⁺).

Example 46

Pharmacological Tests

The following tests were carried out in order to determine the activity of the compounds of formula (I).
Radioligand Binding Assay
The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl₂, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 μM, more particularly of 1 nM to 3 μM and most particularly of 1 nM to 100 nM.

The compounds according to formula I have an activity in the above assay (Ki) particularly of 0.5 nM to 10 μM, more particularly of 0.5 nM to 3 μM and most particularly of 0.5 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% $NaN_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.1 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

All compounds according to the invention are CB2 agonists with $EC_{50}$ below 3 uM, particularly below 1uM, more particularly below 0.5 uM, and selectivity versus CB1 in the corresponding assay of at least 10 fold.

For example, the following compounds showed the following human $EC_{50}$ values (expressed in uM) in the functional cAMP assay described above:

| Example | Ec50:CB1 - hu cAMP | Ec50:CB2 - hu cAMP |
|---|---|---|
| 1 | >10 | 0.0694 |
| 2 | >10 | 0.0716 |
| 3 | >10 | 0.3303 |
| 4 | >10 | 0.4447 |
| 5 | >10 | 0.2211 |
| 6 | >10 | 0.4 |
| 7 | >10 | 0.1801 |
| 8 | >10 | 0.2766 |
| 9 | >10 | 0.2652 |
| 10 | >10 | 0.2612 |
| 11 | >10 | 0.0232 |
| 12 | >10 | 0.0186 |
| 13 | >10 | 0.0194 |
| 14 | >10 | 0.082 |
| 15 | >10 | 0.0115 |
| 16 | >10 | 0.054 |
| 17 | >10 | 0.0146 |
| 18 | >10 | 0.0046 |
| 19 | >10 | 0.0706 |
| 20 | >10 | 0.2725 |
| 21 | >10 | 0.0199 |
| 22 | >10 | 0.0264 |
| 23 | >10 | 0.0159 |
| 24 | >10 | 0.0421 |
| 25 | >10 | 0.1632 |
| 26 | >10 | 0.0104 |
| 27 | >10 | 0.0066 |
| 28 | >10 | 0.0557 |
| 29 | >10 | 0.0296 |
| 30 | >10 | 0.0043 |
| 31 | >10 | 0.0289 |
| 32 | >10 | 0.0062 |
| 33 | >10 | 0.0213 |
| 34 | >10 | 0.0072 |
| 35 | >10 | 0.1221 |
| 36 | >10 | 0.0272 |
| 37 | >10 | 0.0067 |
| 38 | >10 | 0.0024 |
| 39 | >10 | 0.0176 |
| 40 | >10 | 0.5937 |
| 41 | >10 | 0.4923 |
| 42 | >10 | 0.0221 |
| 43 | >10 | 0.0822 |
| 44 | >10 | 0.0589 |
| 45 | >10 | 0.0417 |

β-Arrestin Translocation Assay-PathHunter™ (DiscoveRx)

PathHunter™ β-arrestin CHO-K1 CNR1 cell line (catalog number #93-0200C2) and the β-arrestin CHO-K1 CNR2 cell line (catalog number #93-0706C2) were purchased from DiscoveRx Corporation. The cell line was engineered to express the β-galactosidase EA fragment fused to β-arrestin and the ProLink complementary peptide fused to the target receptor. The PathHunter™ protein complementation assay (DiscoveRx Corporation #93-0001) was performed according to the manufacturer's protocol. Assay plates were seeded containing 7500 (CNR1) and 10000 (CNR2) cells in 384 well plates (Corning Costar #3707, white, clear bottom) in 204 cell plating reagent 2 (Discoverx #93-0563R2A). After incubation at 37° C. (5% $CO_2$, 95% relative humidity) overnight, 5 μl of test compound was added (1% final DMSO concentration) and the incubation continued at 30° C. for 90 min. Detection reagent (12 μl) was then added and the incubation continued at room temperature for 60 min. Plates were then analyzed for a chemiluminescent signal using a Victor $^3$V reader (Perkin Elmer).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

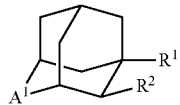

(I)

wherein
$A^1$ is —$CH_2$— or —C(O)—;
one of $R^1$ and $R^2$ is hydrogen and the other one is -$A^2$-C(O)—$R^3$;
$A^2$ is —NH— or absent;
$R^3$ is (A), (B) or (C);

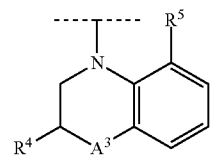

(A)

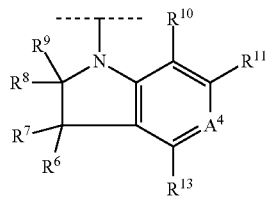

(B)

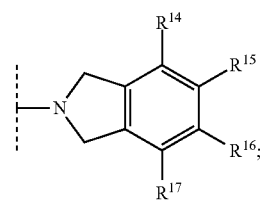

(C)

$A^3$ is —$CR^{18}R^{19}$—, —$NR^{20}$— or —C(O)—;
$A^4$ is nitrogen or —$CR^{12}$—;
$R^4$ is hydrogen or alkoxycarbonyl;
$R^5$ is hydrogen or alkyl;
$R^6$ and $R^7$ are independently selected from hydrogen and alkyl;
$R^8$ and $R^9$ are independently selected from hydrogen and alkyl;
$R^{10}$, $R^{11}$, $R^{12}$ and $R^{13}$ are independently selected from hydrogen, alkyl, nitro, fluoro, chloro, haloalkyl and alkoxy, provided that they are not all hydrogen at the same time;
or $R^{13}$ is alkoxycarbonyl and $R^{10}$, $R^{11}$ and $R^{12}$ are all hydrogen at the same time;
or $R^{10}$, $R^{11}$, $R^{12}$ and $R^{13}$ are all hydrogen at the same time, provided that:
at least two of $R^6$, $R^7$, $R^8$ and $R^9$ are alkyl and the other ones are hydrogen;
or $A^1$ is —C(O)—;
or $R^1$ is hydrogen and $R^2$ is is -$A^2$-C(O)—$R^3$;
$R^{14}$ and $R^{17}$ are independently selected from hydrogen and halogen;
$R^{15}$ and $R^{16}$ are independently selected from hydrogen, morpholinyl and halogen;
one of $R^{18}$ and $R^{19}$ is hydrogen and the other one is independently selected from alkylaminocarbonyl, hydroxyalkyl, alkyl, alkoxy and alkoxyalkoxy;
or one of $R^{18}$ and $R^{19}$ is hydroxyalkyl and the other one is alkyl;

or R$^{18}$ and R$^{19}$ are both hydrogen at the same time, provided that R$^4$ is alkoxycarbonyl or R$^5$ is alkyl; and R$^{20}$ is alkyl;

or a pharmaceutically acceptable salt thereof.

2. A compound according to claim 1, wherein A$^1$ is —CH$_2$—.

3. A compound according to claim 1, wherein R$^1$ is -A$^2$-C(O)—R$^3$ and R$^2$ is hydrogen.

4. A compound according to claim 1, wherein A$^3$ is —CR$^{18}$R$^{19}$— or —NR$^{20}$-.

5. A compound according to claim 1, wherein
one of R$^{18}$ and R$^{19}$ is hydrogen and the other one is independently selected from tert-butylaminocarbonyl, hydroxymethyl, isopropyl, methoxy, ethoxy, isopropoxy, n-butoxy and methoxyethoxy;
or one of R$^{18}$ and R$^{19}$ is hydroxymethyl and the other one is isopropyl;
or R$^{18}$ and R$^{19}$ are both hydrogen at the same time, provided that R$^4$ is methoxycarbonyl or R$^5$ is methyl.

6. A compound according to claim 1, wherein one of R$^{18}$ and R$^{19}$ is hydrogen and the other one is methoxyethoxy or n-butoxy.

7. A compound according to claim 1, wherein R$^{20}$ is methyl or isopropyl.

8. A compound according to claim 1, wherein R$^6$ and R$^7$ are independently selected from hydrogen and methyl.

9. A compound according to claim 1, wherein R$^8$ and R$^9$ are independently selected from hydrogen and methyl.

10. A compound according to claim 1, wherein R$^{10}$ is hydrogen, alkyl or alkoxy, and R$^{11}$, R$^{12}$ and R$^{13}$ are independently selected from hydrogen, alkyl, nitro, fluoro, chloro, haloalkyl and alkoxy, provided that R$^{10}$, R$^{11}$, R$^{12}$ and R$^{13}$ are not all hydrogen at the same time.

11. A compound according to claim 1, wherein R$^{11}$ is hydrogen, nitro, halogen, alkyl or haloalkyl, and R$^{10}$, R$^{12}$ and R$^{13}$ are independently selected from hydrogen, alkyl, nitro, fluoro, chloro, haloalkyl and alkoxy, provided that R$^{10}$, R$^{11}$, R$^{12}$ and R$^{13}$ are not all hydrogen at the same time.

12. A compound according to claim 1, wherein R$^{12}$ is hydrogen, halogen, nitro or alkyl, and R$^{10}$, R$^{11}$ and R$^{13}$ are independently selected from hydrogen, alkyl, nitro, fluoro, chloro, haloalkyl and alkoxy, provided that R$^{10}$, R$^{11}$, R$^{12}$, and R$^{13}$ are not all hydrogen at the same time.

13. A compound according to claim 1, wherein R$^{13}$ is hydrogen, halogen, alkyl or alkoxy, and R$^{10}$, R$^{11}$ and R$^{12}$ are independently selected from hydrogen, alkyl, nitro, fluoro, chloro, haloalkyl and alkoxy, provided that R$^{10}$, R$^{11}$, R$^{12}$ and R$^{13}$ are not all hydrogen at the same time.

14. A compound according to claim 1, wherein R$^{14}$ and R$^{17}$ are independently selected from hydrogen and fluoro.

15. A compound according to claim 1, wherein R$^{15}$ and R$^{16}$ are independently selected from hydrogen, fluoro, chloro and morpholinyl.

16. A compound according to claim 1 selected from
1-(Adamantane-1-carbonyl)-2,3-dihydro-1H-quinolin-4-one;
1-(Adamantane-1-carbonyl)-1,2,3,4-tetrahydro-quinoline-4-carboxylic acid tert-butylamide;
1-(Adamantane-1-carbonyl)-1,2,3,4-tetrahydro-quinoline-3-carboxylic acid methyl ester;
Adamantan-1-yl-(4-hydroxymethyl-4-isopropyl-3,4-dihydro-2H-quinolin-1-yl)-methanone;
Adamantan-1-yl-(8-methyl-3,4-dihydro-2H-quinolin-1-yl)-methanone;
Adamantan-1-yl-(4-ethoxy-3,4-dihydro-2H-quinolin-1-yl)-methanone;
Adamantan-1-yl-(6-nitro-2,3-dihydro-indol-1-yl)-methanone;
Adamantan-1-yl-(5-nitro-2,3-dihydro-indol-1-yl)-methanone;
Adamantan-1-yl-(4,6-difluoro-2,3-dihydro-indol-1-yl)-methanone;
Adamantan-1-yl-(6-trifluoromethyl-2,3-dihydro-indol-1-yl)-methanone;
Adamantan-1-yl-(5-fluoro-2,3-dihydro-indol-1-yl)-methanone;
Adamantan-1-yl-(4-chloro-2,3-dihydro-pyrrolo[3,2-c]pyridin-1-yl)-methanone;
Adamantan-1-yl-(1,3-dihydro-isoindol-2-yl)-methanone;
Adamantan-1-yl-(7-methoxy-2,3-dihydro-indol-1-yl)-methanone;
Adamantan-1-yl-(3,3-dimethyl-2,3-dihydro-indol-1-yl)-methanone;
1-(Adamantane-1-carbonyl)-2,3-dihydro-1H-indole-4-carboxylic acid methyl ester;
Adamantan-1-yl-(2,3-dimethyl-2,3-dihydro-indol-1-yl)-methanone;
Adamantan-1-yl-(5-methyl-2,3-dihydro-indol-1-yl)-methanone;
Adamantan-1-yl-(6-methyl-2,3-dihydro-indol-1-yl)-methanone;
Adamantan-1-yl-(7-methyl-2,3-dihydro-indol-1-yl)-methanone;
Adamantan-1-yl-(4-methoxy-2,3-dihydro-indol-1-yl)-methanone;
Adamantan-1-yl-(4-methyl-2,3-dihydro-indol-1-yl)-methanone;
Adamantan-1-yl-(4-methyl-3,4-dihydro-2H-quinoxalin-1-yl)-methanone;
Adamantan-1-yl-(4-isopropyl-3,4-dihydro-2H-quinoxalin-1-yl)-methanone;
Adamantan-1-yl-[4-(2-methoxy-ethoxy)-3,4-dihydro-2H-quinolin-1-yl]-methanone;
Adamantan-1-yl-(4-butoxy-3,4-dihydro-2H-quinolin-1-yl)-methanone;
Adamantan-1-yl-(4-isopropoxy-3,4-dihydro-2H-quinolin-1-yl)-methanone;
Adamantan-1-yl-(4-methoxy-3,4-dihydro-2H-quinolin-1-yl)-methanone;
Adamantan-2-yl-(2,3-dihydro-indol-1-yl)-methanone;
Adamantan-1-yl-(5,6-difluoro-2,3-dihydro-indol-1-yl)-methanone;
5-(2,3-Dihydro-indole-1-carbonyl)-adamantan-2-one;
(2,3-Dihydro-indol-1-yl)-(3-hydroxy-adamantan-1-yl)-methanone;
1,3-Dihydro-isoindole-2-carboxylic acid adamantan-1-ylamide;
Adamantan-1-yl-(5-chloro-6-morpholin-4-yl-1,3-dihydro-isoindol-2-yl)-methanone;
Adamantan-1-yl-(4-fluoro-1,3-dihydro-isoindol-2-yl)-methanone; and
Adamantan-1-yl-(5-fluoro-1,3-dihydro-isoindol-2-yl)-methanone.

17. A compound according to claim 1 selected from
Adamantan-1-yl-(5-fluoro-2,3-dihydro-indol-1-yl)-methanone;
Adamantan-1-yl-(4-isopropyl-3,4-dihydro-2H-quinoxalin-1-yl)-methanone;

Adamantan-1-yl-(4-butoxy-3,4-dihydro-2H-quinolin-1-yl)-methanone; and

Adamantan-2-yl-(2,3-dihydro-indol-1-yl)-methanone.

18. A process for the preparation of a compound of formula (I) as defined in claim 1 comprising one of the following steps:

(a) The reaction of a compound of formula (D)

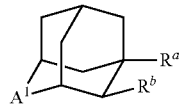

(D)

in the presence of $R^3$—H and a base; or (b) The reaction of a compound of formula (E)

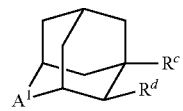

(E)

in the presence of $R^3$—H and a base;
wherein
one of $R^a$ and $R^b$ is hydrogen and the other one is —COOH or —COCl;
one of $R^c$ and $R^d$ is hydrogen and the other one is —N=C=O;
and wherein $A^1$ and $R^3$ are as defined in claim 1.

19. A compound prepared by a process according to claim 18.

20. A pharmaceutical composition comprising a compound according to claim 1.

21. A method for the treatment of pain, which method comprises administering an effective amount of a compound as defined in claim 1 to a patient in need thereof.

22. The method of claim 21, wherein the pain is selected from chronic pain, atherosclerosis, regulation of bone mass, inflammation, ischemia, reperfusion injury, fibrosis, chronic kidney diseases, heart diseases, autoimmune diseases, graft versus host diseases, burning, hypertrophic scars, keloids, gingivitis, liver cirrhosis, tumors, pyrexia and thermal injury.

23. The method of claim 21, wherein the pain is selected from systemic fibrosis, liver fibrosis, lung fibrosis, kidney fibrosis, systemic sclerosis, kidney fibrosis, chronic allograft nephropathy, diabetic nephropathy, hypertensive nephropaty, lupus nephritis, glomerulonephropathy, angina pectoris, cardiomyopathy, heart failure, myocardial infarction, rheumatoid arthritis and systemic lupus erythematosus.

* * * * *